United States Patent
Wulfman

(10) Patent No.: US 10,092,313 B2
(45) Date of Patent: Oct. 9, 2018

(54) MEDICAL SEALED TUBULAR STRUCTURES

(75) Inventor: Edward I Wulfman, Woodinville, WA (US)

(73) Assignee: BOSTON SCIENTIFIC LIMITED (BM)

( * ) Notice: Subject to any disclaimer, the term of this patent is extended or adjusted under 35 U.S.C. 154(b) by 2002 days.

(21) Appl. No.: 10/798,601

(22) Filed: Mar. 10, 2004

(65) Prior Publication Data
US 2004/0230212 A1 Nov. 18, 2004

Related U.S. Application Data

(60) Provisional application No. 60/453,846, filed on Mar. 10, 2003.

(51) Int. Cl.
*A61B 17/3207* (2006.01)
*A61B 5/06* (2006.01)
(Continued)

(52) U.S. Cl.
CPC .... *A61B 17/320758* (2013.01); *A61B 1/0057* (2013.01); *A61B 1/00071* (2013.01); *A61B 5/061* (2013.01); *A61B 5/415* (2013.01); *A61B 5/418* (2013.01); *A61B 17/320725* (2013.01); *A61M 39/06* (2013.01); *A61B 1/01* (2013.01); *A61B 8/12* (2013.01); *A61B 8/4209* (2013.01); *A61B 17/32002* (2013.01); *A61B 17/3462* (2013.01); *A61B 2017/00017* (2013.01); *A61B 2017/00199* (2013.01); *A61B 2017/00973* (2013.01); *A61B 2017/22049* (2013.01);
(Continued)

(58) Field of Classification Search
CPC ............ A61B 2017/2905; A61B 2017/320032
USPC .................................................. 606/170, 180
See application file for complete search history.

(56) References Cited

U.S. PATENT DOCUMENTS

| | | | |
|---|---|---|---|
| 4,445,509 A | 5/1984 | Auth | |
| 4,857,045 A | 8/1989 | Rydell | |

(Continued)

FOREIGN PATENT DOCUMENTS

| | | |
|---|---|---|
| EP | 1 382 366 A1 | 1/2004 |
| WO | 2005/004965 A2 | 1/2005 |

*Primary Examiner* — Katherine M Shi
*Assistant Examiner* — Michael Mendoza
(74) *Attorney, Agent, or Firm* — Seager, Tufte & Wickhem LLP

(57) ABSTRACT

A tubular structure comprising multiple overlapping layers surrounding a lumen has flexibility and structural integrity by allowing portions of the layers to slip relative to each other. One embodiment includes a support layer having a wired coil, braid or weave support element underlies at least one overlying layer. The support layer is fixed to the overlying layer at a bonding point and the remaining portion of the support layer is not fixed to the overlying layer, i.e. "free portion". The support layer is permitted to slip at the free portion of the support layer, relative to the overlying layer. Further flexibility may be provided by a coil element of the support layer having substantial gaps between the loops of the coil to impart high flexibility of the tubular structure. In one embodiment, an etched sheath is heat shrunk around an underlying layer with a shrink ratio of 25 percent or less of its original diameter, such that the etchings are at least substantially preserved through the shrinkage process.

25 Claims, 5 Drawing Sheets

(51) Int. Cl.
*A61B 5/00* (2006.01)
*A61M 39/06* (2006.01)
*A61B 1/00* (2006.01)
*A61B 1/005* (2006.01)
*A61B 1/01* (2006.01)
*A61B 8/12* (2006.01)
*A61B 8/00* (2006.01)
*A61B 17/32* (2006.01)
*A61B 17/34* (2006.01)
*A61B 17/00* (2006.01)
*A61B 17/22* (2006.01)
*A61B 17/29* (2006.01)

(52) U.S. Cl.
CPC ............... *A61B 2017/2927* (2013.01); *A61B 2017/320032* (2013.01); *A61B 2217/005* (2013.01); *A61M 39/0606* (2013.01)

(56) References Cited

U.S. PATENT DOCUMENTS

| | | | |
|---|---|---|---|
| 5,181,920 A * | 1/1993 | Mueller | A61B 17/3207 604/22 |
| 5,308,354 A * | 5/1994 | Zacca et al. | 606/159 |
| 5,454,795 A * | 10/1995 | Samson | A61L 29/041 600/435 |
| 5,501,694 A * | 3/1996 | Ressemann et al. | 606/159 |
| 5,527,325 A * | 6/1996 | Conley et al. | 606/159 |
| 5,527,326 A * | 6/1996 | Hermann et al. | 606/159 |
| 5,769,828 A | 6/1998 | Jonkman | |
| 5,795,325 A | 8/1998 | Valley et al. | |
| 5,853,400 A | 12/1998 | Samson | |
| 5,868,767 A | 2/1999 | Farley et al. | |
| 5,938,670 A | 8/1999 | Keith et al. | |
| 6,048,338 A | 4/2000 | Larson et al. | |
| 6,078,831 A * | 6/2000 | Belef | A61B 8/12 600/424 |
| 6,080,170 A | 6/2000 | Nash et al. | |
| 6,080,171 A | 6/2000 | Keith et al. | |
| 6,143,013 A * | 11/2000 | Samson et al. | 606/192 |
| 6,197,014 B1 | 3/2001 | Samson et al. | |
| 6,270,477 B1 * | 8/2001 | Bagaoisan et al. | 604/96.01 |
| 6,464,684 B1 | 10/2002 | Galdonik | |
| 6,562,021 B1 | 5/2003 | Derbin et al. | |
| 6,565,588 B1 | 5/2003 | Clement et al. | |
| 6,626,853 B2 | 9/2003 | White et al. | |
| 6,638,245 B2 | 10/2003 | Miller et al. | |
| 7,235,088 B2 * | 6/2007 | Pintor | A61B 17/320758 606/159 |
| 7,879,022 B2 | 2/2011 | Bonnette et al. | |
| 2002/0007190 A1 | 1/2002 | Wulfman et al. | |
| 2004/0006358 A1 | 1/2004 | Wulfman et al. | |
| 2005/0059957 A1 | 3/2005 | Campbell et al. | |
| 2008/0097298 A1 * | 4/2008 | Fisher | A61B 17/320758 604/103.04 |

* cited by examiner

MEDICAL SEALED TUBULAR STRUCTURES

CROSS-REFERENCE TO RELATED APPLICATIONS

This application claims priority from U.S. Provisional Patent Application No. 60/453,846, filed Mar. 10, 2003. The disclosure of this application is incorporated herein by reference in its entirety.

FIELD OF THE INVENTION

The present invention relates to a sealed tubular structure having multiple generally co-axial layers useful in the medical field. In particular, the invention relates to a tubular structure having a support layer that is slippable relative to an overlying layer to provide varying degrees of flexibility. The present invention is particularly useful for providing a sealed lumen in the medical field. It is to be understood that the terms "medical field" and "medical device", as used herein, include traditional medicine as well as alternative medicines including chiropractic, acupuncture, etc., as well as the veterinary field.

BACKGROUND

In numerous applications of devices in the medical field, a tubular structure having a sealed lumen along its length may be a necessary or desirable component of the device. It is often useful for the sealed tubular structure to have a variety of characteristics in order to be adaptable for different applications. At times, it is also important for the sealed tubular structure to have different characteristics and construction along the length of the tubular structure. Different characteristics of the tubular structure may be provided by including multiple layers of material that overlap with each other and form the tube wall.

Some medical devices incorporate a tubular structure in the form of a catheter having an internal lumen for transporting material, fluid, and/or suction pressure between the ends of the catheter. The catheter walls effectively seal the lumen to prevent liquid or gasses, including air, from contacting certain device elements, entering the body through the device, seeping in such as where suction pressure may be diluted, or leaking out of the device such as where suction pressure may be lost.

Intracorporeal medical devices having catheters are employed for therapeutic and/or diagnostic procedures. Different types of catheters have different levels of flexibility to enable the catheter to deliver material to and remove material from an internal body site. Guide catheters are placed in a patient to guide another device to a target internal body site. Operating catheters are used to deliver a device, such as a stent, an angioplasty device, an atherectomy or thrombectomy device, or the like, to the target internal body site.

In some particular applications of a catheter, atherectomy or thrombectomy devices are used for treatment of arterial occlusions. Atherosclerosis is a condition arising from the deposition of fat-like matter, i.e. plaque, on the walls of blood vessels. As a result of accumulated obstructions, blood flow becomes restricted or blocked, creating health risks, including coronary artery disease, angina and heart attacks. Most methods of using atherectomy and thrombectomy devices involve placement of a guiding catheter into the body and insertion of a guidewire, over which an operating head is guided to a target site where an occlusion is located within a blood vessel. However, devices that do not employ guidewires are also possible. The catheter surrounds a drive shaft to effectively isolate the rotating elements of the device from direct contact with any healthy body matter, e.g. tissue. The drive shaft is coupled to an operating head that is advanced, and in some devices, rotated to cut or ablate the obstruction and to restore or improve blood flow in the vessel.

Regardless of the particular application for the tubular structure, problems which must be overcome to establish a sealed tubular structure are particularly difficult when at least portions of the tube is required to be highly flexible. Flexibility of sections of a catheter is of specific concern where an intracorporeal medical device must be routed along a tortuous path, such as through blood vessels and various internal structures, before placement at the target site. An obstructed blood vessel, for instance, may be located in peripheral vessels, coronary vessels, cranial vessels, or other areas. For example, where the target site is in a femoral vessel, such as in a groin region, the catheter may be introduced into one leg, e.g. a retrograde stick, and guided in an upward direction, around a sharp angle in the torso and down again towards the opposite leg having the injury. In this particular case, the catheter should have at least a highly flexible end and middle portion to negotiate the sharp curvature in the path. However, the catheter must also include some stiffness to permit the catheter to be pushed into the body. Thus, not only should the layers of the tubular structure be sealed, but also permit varying levels of flexibility along at least portions of the tubular structure.

A further concern of a tubular structure is that the structure may kink where the structure must be formed around a sharp curve or bend. Infusion or withdrawal of liquids through the lumen of the tubular structure may be required during operation of a device. In this case, the tubular structure must have sufficient stiffness to resist collapse or enlarge of the lumen under a range of pressures and force conditions. For example, a wall of a catheter that caves in due to flexing may significantly block the lumen space and decrease transport within the lumen. Thus, it is essential that tubular structures used in connection with such devices be as flexible as possible during placement and removal, yet have a high degree of structural integrity for operation of the device.

Some previous attempts at designing a kink-resistive tubular structure provided a layer of a coiled, braided or otherwise weaved member that has tight loops and that is fixedly attached to or embedded in a polymeric layer, such as a polyimide or plastic layer. Although the construction of the layer may allow for a small amount of flexibility, the use of a weaved or coiled layer attached to or embedded in a polymeric layer generally results in a tubular structure that is stiffer in portions of the structure than which is required by many applications. Some tubular structure designs that include such layers are described in U.S. Pat. Nos. 6,464,684; 6,197,014; and 5,868,767.

Another challenge in forming a layered tubular structure is in creating close and reliable contact between multiple flexible layers, such that one layer encases another layer and is permanently affixed to at least a portion of the other layer. One current construction of a tubular structure having multiple layers includes a layer of thermally shrinkable material overlapped with an inner layer. Heat is applied to melt and shrink the thermally shrinkable layer into contact with the inner layer. In this manner, the thermally shrinkable layer molds to the underlying layer, but does not necessarily bond to the underlying layer.

Thus, although conventional thermally shrinkable material forms closely overlapped layers, the layer may not be sufficiently bonded to create a sealed tubular structure in a manner that is durable and reliable and can be used under a variety of pressure and force requirements. For example, fluoropolymer plastics, such as polytetrafluoroethylene (PTFE), e.g. TEFLON material (from i.e. Dupont DeNemours Corp., in Wilmington, Del.) are sometimes included in the thermally shrinkable layer to reduce friction as the tubular structure is guided through the body. Unfortunately, the lubricity of fluoropolymers makes it generally difficult to bond the fluoropolymer to other layers by using conventional methods and adhesives.

Some efforts to bond fluoropolymer layers that are not thermally shrinkable include etching the surface of the fluoropolymer to change the surface characteristics and make the layer "sticky". Although etching has generally been useful for bonding non-thermally shrinkable material that includes fluoropolymer plastics, the etching technique has not typically been applied to the surface of thermally shrinkable material for bonding. In general, the process of heating thermally shrinkable material is thought to melt the etchings on the material surface to such as great extent that the etchings are rendered useless for bonding.

The present invention is directed to improved tubular structures in which thermally shrinkable materials are closely associated with other layer(s) to provide a sealed tubular structure that is flexible, kink-resistant, and has a high degree of structural integrity. The present invention fulfills these needs and provides further related advantages.

SUMMARY

A tubular structure that has flexibility while also maintaining its structural integrity is provided. The tubular structure has multiple layered walls that define an internal lumen extending along the length of the structure to serve as a passageway. A support layer may be provided having a support element, such as a continuous coil a braid element or a weave element including a plurality of loops. The support layer is bonded to an overlying layer at a bonding point and is not bonded to the overlying layer at the remaining portion of the support layer. As the structure is bent, the free portion of the support layer slips relative to the overlying layer. In this manner, the tubular structure resists kinking of the tubular structure and impeding the lumen space extending through the structure.

At times, more flexibility is desired and the support layer includes a plurality of substantial gaps between each loop of the support element. The gaps are of sufficient size to resist kinking of the tubular structure. The length of substantial gaps is about 10-200 percent of the width of the wire. 17. The amount of flexibility that may be provided by this highly flexible area having substantial gaps in the support element and slipping of layers may be allow the structure to bend around a 0.25 to 0.50 radius object without kinking. At other times, only medium flexibility is required. For example, the structure is flexible around a 0.75 to 1.50 radius object without kinking. In this case, no or little gaps may be provided between loops of the support element.

In one embodiment, one layer of the tubular structure is an etched thermally shrinkable sheath that is shrunk in a manner that preserves etchings and permits bonding, wherein the etchings do not melt during the shrinkage process so significantly as to not be useful. The sheath may encase at least a portion of the underlying layer by heat-reduction of 25 percent or less of an original diameter of the sheath to at least substantially maintain the etches during the heat-reduction. In one embodiment, a portion of the shrinkable sheath is bonded to a metallic underlying layer and another portion of the sheath is free to slip over the underlying layer when bent. The sheath comprises a polytetrafluoroethylene material, such as PTFE, TEFLON material, FEP and/or PFA.

Methods of constructing a medical tubular structure having a shrinkable sheath layer are also provided in which etches are produced in the interior surface of a thermally shrinkable tube comprising a polytetrafluorothylene material. The tube is heated for sufficient temperature and length of time to reduce the sheath around an underlying layer by 25 percent or less in diameter of an original diameter of the sheath whereby etchings are substantially preserved during the heating. The resulting etchings are sufficient to provide sites for easy bonding of a lubricious sheath layer to another layer. In order to reduce any friction created during the heating, the sheath is rubbed across an arched surface with sufficient force to break up the friction between the loops of the coil element and the sheath. In one embodiment, at least one of opposing ends of the sheath is bonded to the underlying layer to permit slipping of the sheath along the underlying layer between the opposing ends of the sheath.

BRIEF DESCRIPTION OF THE DRAWINGS

The present invention is illustrated by way of example in the figures of the accompanying drawings and the figures are not intended for limitation, which figures are not intended to limit the present invention, and in which:

FIGS. 1A-1C are schematic diagrams, in magnification, of cross-sections of the at least portions of the tubular structure having multiple layers, according to one embodiment of the invention, wherein FIG. 1A shows the free portion of a support layer permitted to slip relative to an overlying layer, FIG. 1B shows a thermally shrinkable sheath bonded at one end and slippable over a coiled underlying layer, FIG. 1C shows a thermally shrinkable sheath between an underlying layer and upper layer;

DETAILED DESCRIPTION

A tubular structure comprising a lumen surrounded by overlapping multiple layers is provided. A support layer having a wired coil, braid or weave support element underlies at least one overlying layer. The support layer is fixed to the overlying layer at a bonding point and the remaining portion of the support layer is not fixed to the overlying layer, i.e. "free portion". The support layer is permitted to slip at the free portion of the support layer, relative to the overlying layer. In this manner, the tubular structure avoids kinking as the structure becomes bent. Further flexibility may be provided in one case by a coil element of the support layer having substantial gaps between the loops of the coil to impart high flexibility of the tubular structure. In any case, the tubular structure may have a composite construction with distinctly different sections along its length.

In one embodiment, at least a section of the tubular structure includes an etched sheath that is heat shrunk around an underlying layer to closely contact the underlying layer. The sheath has a shrink ratio of 25 percent or less of its original diameter, such that the etchings are at least substantially preserved through the shrinkage process. A bonding point on the sheath is fixed to the underlying layer, such as the support layer, and/or to other component, and the etchings facilitate adherence of the shrinkable sheath at the bonded point but also permit slippage.

Figure 1A:
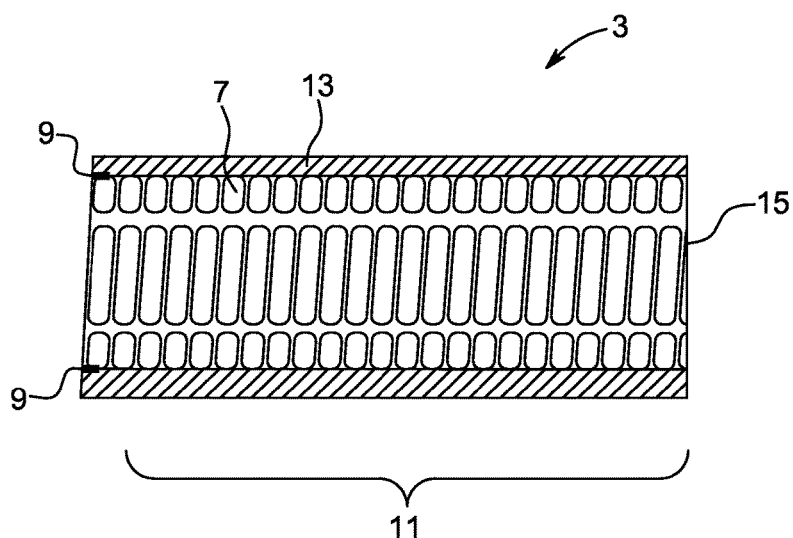
Figure 1B:
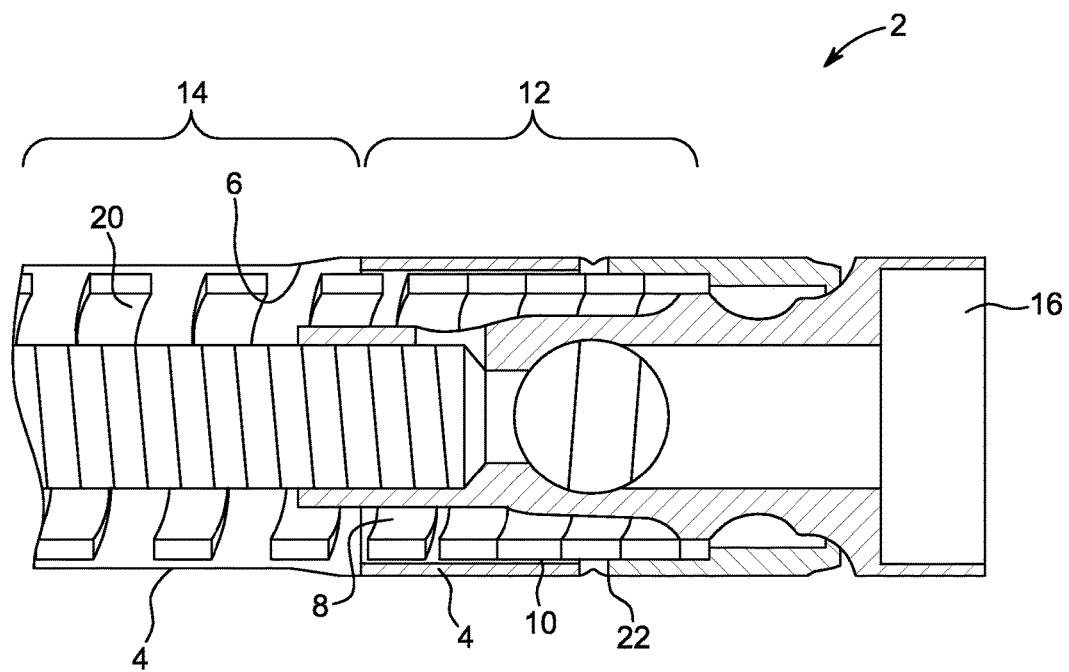
Figure 1C:
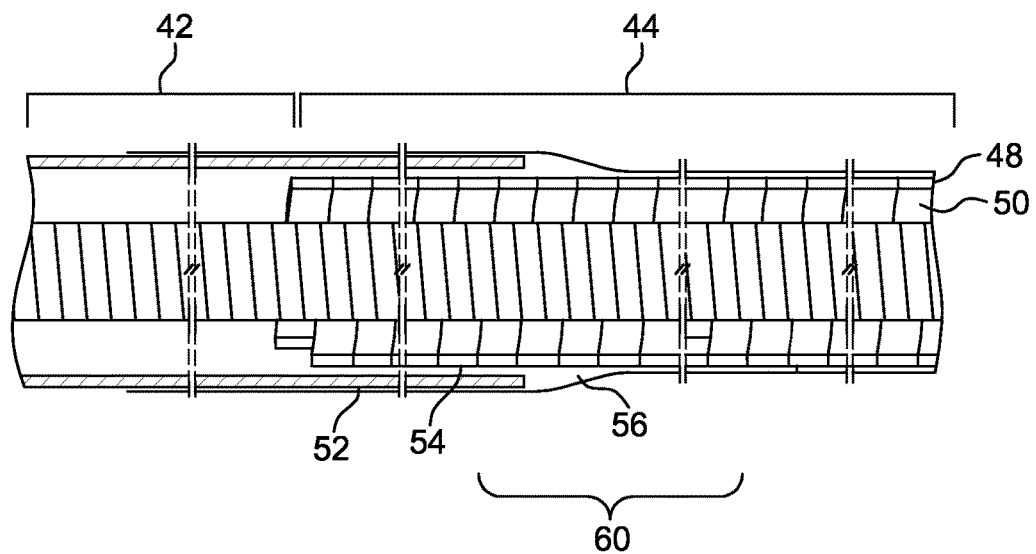

Some variations of the tubular structure and/or discrete sections of the tubular structure, according to the present invention, are depicted variously in FIGS. 1A to 1C. The tubular structure may include one or any combination of the variations shown in FIGS. 1A to 1C, or any combination of the characteristics of these variations. In general, the tubular structure includes a support layer having a bonding point to at least one overlying layer and a free portion being slippable relative to the overlying layer. The support element may be integrated with the overlying layer in a loose enough manner to slip when needed without being fixedly embedded. The bonding point allows the support layer to attach to the overlying layer and allows the remaining portion of the support layer to be free.

As shown by the tubular structure construct 3 in FIG. 1A, a support layer 7 is bonded to an overlying layer 13 at a bonding point 9 and has a free portion 11 that is not embedded or otherwise attached to the overlying layer. The support layer 7 is shown as a support element comprising one or more wire(s) formed into multiple spaced loops along the length of the support layer. The support element may be a contiguous coil, braid and/or weave support element, and the like, or combinations thereof. In particular, the support element may comprise a continuous length spiral wire that forms a coil and has a plurality of spaced loops along the length of the support element formed by each spiral of the wire along the coil. In one embodiment, the support element may be a metallic wire or ribbon. The wire may have any convenient dimensions to fit within the tubular structure. In one embodiment, the wire is about 0.015 inch wide and about 0.030 inch thick.

In one embodiment, the loops are adjacent to each other when the support layer is in a planar unbent position, whereby very little or no gaps exist between the loops. The loops are not fixed to each other, such that the loops may move and slip in relation to each other, allowing the tubular structure to easily bend and resisting collapse or kink of the tubular structure.

Where the support layer does not overlay any other layer, the inner diameter of the support layer may define the diameter of a lumen 15. The lumen is sealed along its length within the tubular structure walls. The lumen is often open at one or both the ends and may connect with other components of a medical device. The lumen often houses medical device components, such as a drive shaft, guidewire, material, e.g. collagen, etc.

As shown in FIGS. 1B and 1C, one overlying layer may include a thermally shrinkable sheath 4 having etchings (not shown) provided on at least the interior surface 6 of the sheath. The shrinkable sheath may contact various distinct layers of the tubular structure in a variety of different ways. The shrinkable sheath is closely associated with at least a portion of the longitudinal length of one or more underlying layer(s), e.g. support layer, and, at times, an optional overlying layer.

In one embodiment of the tubular structure 2 in a medical device as shown in FIG. 1B, a thermally shrinkable sheath 4, a support layer 8 underneath the sheath and an adhering layer 10 inside the sheath are provided. The tubular structure may have at least bonding region 12, such as one or more ends of the sheath and a highly flexible area 14. The tubular structure may be attached to a component 16 of the medical device to form a junction.

The thermally shrinkable sheath 4 comprises a fluoropolymer plastic that shrinks when exposed to certain temperatures and can be etched, such as PTFE, TEFLON material, FEP, PFA, etc. In many applications it is desirable to use high thermal resistant material that melts at higher temperature, such as PTFE, which melts at about 650 degrees F., whereas FEP melts at between 400 to 500 deg. F. The sheath is very thin, such as 0.001 to 0.002 inch. The etchings may be created by chemical reaction or wet-etching, such as TETRA-ETCH processing (a registered trademark of W.L. Gore & Assoc., Newark, Del.), sodium ammonia etching or by mechanical techniques.

One example of an etching technique involves a chemical reaction in which sodium reacts with fluorine molecules on the surface of the layer, resulting in fluorine molecules being stripped from the carbon backbone of the fluoropolymer. The carbon atoms on the surface are electron deficient and the electrons are restored by exposure to air, oxygen molecules, water vapor or hydrogen. Resulting groups of organic molecules improve the adhesion properties of the material.

In some embodiments, the etchings may be additionally provided on the inner and outer diameter surface. Etches may be provided across the entire length of the surface. In other embodiments, the etchings may also be located at discrete portions of the tubular structure. For example, the etchings may be confined to one or both ends of the tubular structure or other portions of the surface of the thermally shrinkable layer.

The etchings facilitate bonding of the shrinkable sheath with other layers, such as in the bonding region 12. In one embodiment, an adhesive is applied to the bonding region and the etchings create sites for the glue to adhere. Any biocompatible adhesive may be used for these purposes, such as cyanoacrylate glue. The adhesive may be applied to one or both ends of the thermally shrinkable sheath.

The etchings also facilitate bonding without adhesives to layers, such as the adhering layer 10, comprising certain materials that tend to stick to the etched sheath. The adhering layer may be overlying the shrinkable sheath (as shown) or underlying the sheath. Typically, the adhering layer comprises a plastic that is able to withstand the shrinking temperature of the sheath, such as a thermosetting plastic that burn rather than melt when exposed to certain high temperatures. For example, oftentimes the adhering layer comprises polyimid, which withstands heat exposure of up to 660 deg. F. and wherein the shrinkable sheath comprises a material that melts at a temperature lower than 660 deg F., e.g. PTFE. Such plastic may stick with the etched sheath after heating, rather than metals in which the surfaces tend to be slippery.

In one embodiment, the tubular structure includes a highly flexible area in which the sheath is capable of slipping over the underlying support layer when the tubular structure is bent. In this highly flexible area, the support layer comprises a material that does not permit the sheath to adhere to it, such as metal, e.g. steel, through simple contact and without the use of bonding techniques. The portion of the sheath located above the free section of the support layer may or may not include etchings. The support layer comprises a material that permits the shrinkable sheath to slip relative to the underlying layer due to lubriciousness of material comprising the shrinkable sheath. For example, the support layer may comprise steel and the shrinkable sheath may comprise TEFLON material.

In general, the amount of shrinkage that the sheath undergoes is limited by the outer diameter of the underlying layer. In order to preserve the etchings of the shrinkable sheath during the heating process, the underlying layer, e.g. support layer, is no less than 25 percent of the original diameter of the shrinkable sheath diameter prior to the sheath being shrunk around the underlying layer. In other words, the original diameter of the shrinkable sheath is no more than 25 percent of the diameter of the underlying layer.

The thermally shrinkable sheath melts within the interstices of the support element. The interstices may be gaps located between the loops of the support element. The gaps are sized to permit flexibility of the tubular structure and resistance to kinking.

Figure 2:
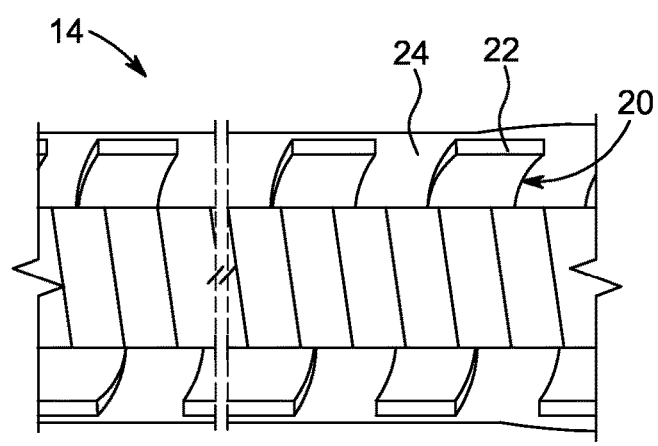
FIG. 2 is a schematic diagram of a cross-section of one embodiment of the support element having multiple loops and gaps between the loops.

In one embodiment of highly flexible area 14 of a tubular structure, as shown in FIG. 2, the support layer 20 includes substantial gaps 24 in the interstices between loops 22. The gaps in this area are about 10-200 percent of the width of the wire of the support element, and more typically about 100-200 percent. For example, where the wire of the support element is 0.15 inch, the gaps may be between about 0.15 to 0.030 inch. Generally, the gap may be between about 0.002 to 0.030 inch and more typically about 0.015 inch. The gaps are not so large as to allow the shrinkable sheath to excessively melt between the gaps, such that the sheath becomes sucked into the lumen of the tubular structure, thereby at least partially occluding the lumen. Furthermore, the gaps are not so large as to compromise the form of the lumen, but yet provide for the required amount of flexibility.

This highly flexible section is capable of bending around sharp curves. In operation, as the tubular structure is bent around a curve, the sheath stretches across the free portion of the support layer. The maximum amount of curvature permitted by the highly flexible area is not so great as to cause the sheath to stretch beyond the elastic limit of the sheath, so that the sheath returns to at least substantially its original orientation as the tubular structure straightens. For example, the high flexibility of this section may permit the tubular structure at this section to bend around an object that is between 0.25 and 0.50 radius without kinking.

By comparison to the highly flexible section, at the bonding region 12, the tubular structure is less flexible because the support layer is bonded to overlying layers and/or other device components 16. Bonding may include by various mechanisms to join the layers, such as adhesive, welding, etc. In one embodiment, the support layer is welded to the component, such as a bearing, operating head, etc. in a manner that preserves the seal around the lumen of the tubular structure. Furthermore, an adhesive may be applied to the adhering layer, shrinkable sheath and/or support layer. In one example, an opening is provided between the tubular structure and the component 16 and glue fills the opening. In this manner, glue contacts the proximal ends of the adhering layer and the support layer without seeping between the shrinkable sheath and the support layer and/or adhering layer. However, in another embodiment, the glue also contacts the upper and/or lower surfaces of the shrinkable sheath.

In some embodiments, the support layer includes a less flexible support element at and/or near the bonding point. The wire loops of the support layer may be welded or glued together to form segment of fixed loops. The stiffness of the support layer permits adhesive at the bonding point to be exposed to shearing forces and be a stronger bond rather than being subjected to peeling forces where the adhesive may be more prone to separate from the support layer. The less flexible area near the bonding point may be any length that is necessary or desired to add strength and secure the tubular structure to the component 16, and usually the area is a short distance from the junction of the tubular structure with another medical device component Another variation of a tubular structure 40 or portion thereof, is also shown, by example, in FIG. 1C to demonstrate further option characteristics a tubular structure. Furthermore, a semi flexible section 44 may be provided with more stiffness than the highly flexible section described with regard to FIG. 1B. The semi flexible section 44 may include a support layer 48 with a support element 50 having no or very small gaps between loops of the support element. The semi flexible section may further include one or more outer layers to increase the stiffness of this section, where desired. Another layer may be an attachment layer 52 that provides extra support to the tubular structure. The attachment layer may comprise any convenient material, such as polyimid.

In still other embodiments, the tubular structure has one or more further sections of lesser flexibility that does not include a support element of an underlying layer. At a transition area 60 between sections of varying flexibility, multiple thermally shrinkable layers may be included in at least a portion of the longitudinal length of the tubular structure wall. For example, a shrinkable insert 54 may be provided between the support layer and the shrinkable sheath 56 at the transition area 60 between levels of stiffness. The shrinkable insert may be positioned under the attachment layer 52 and over the support layer 48. Further, the shrinkable sheath may be positioned over the attachment layer. The two shrinkable layers sandwich the attachment layer and extend beyond the proximal end of the attachment layer. In this manner, the shrinkable insert serves as a strain relief to provide a smooth transition of stiffness in the tubular structure and permits resistance to kinking at the transition area as the tubular structure bends. The shrinkable insert also may fill in any gap that may otherwise exist between the attachment layer and underlying layer in the transition area.

The tubular structures with various sections depicted and described are provided by way of example and are not intended to limit the layered tubular structure of the present invention. One or more combinations of these variations may be included within a single tubular structure. The present tubular structure is adaptable and may be used in a variety of medical devices that require a tube with a level of flexibility and support. The tubular structure may comprise a catheter, covered stent, implantable graft, a cannula, etc.

Figure 3:
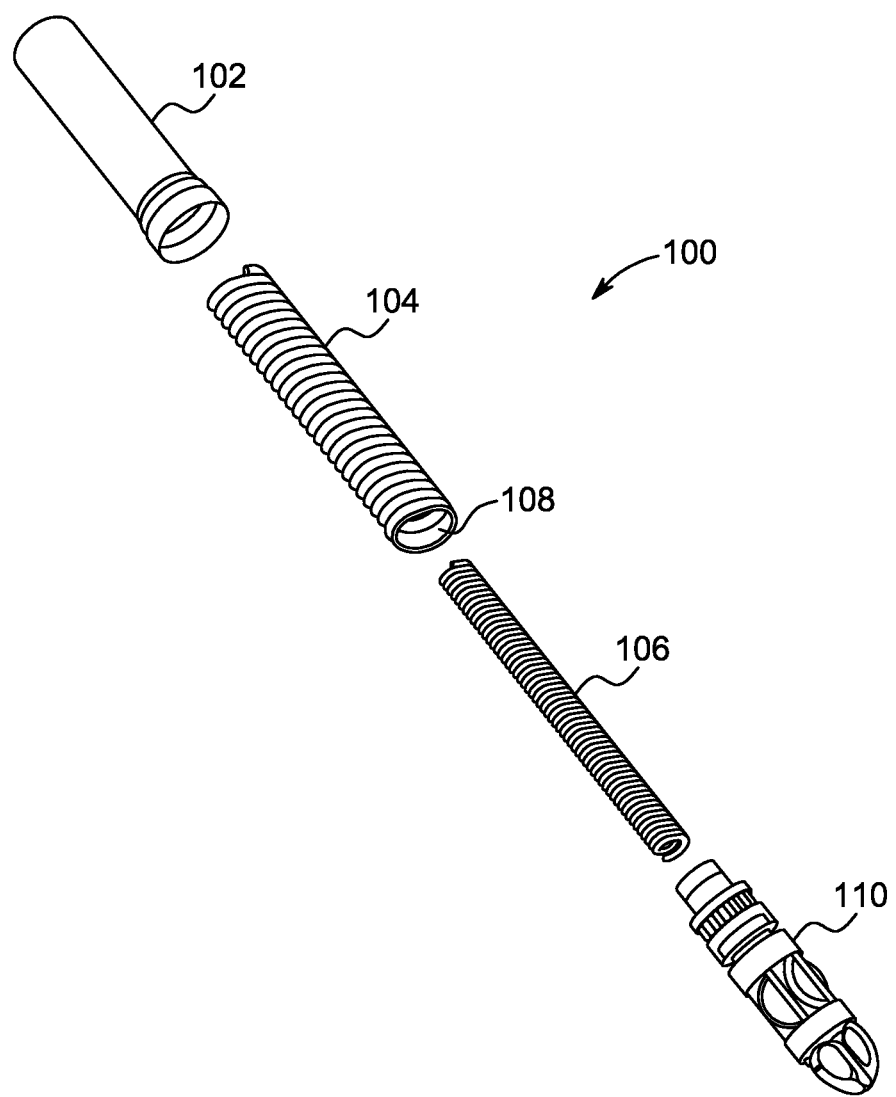
FIG. 3 is a schematic diagram showing an external view of exploded components of the layers of one tubular structure of a catheter.

One particular application of the tubular structure is a catheter construction for an intracorporeal medical device. One embodiment of catheter that incorporates the tubular structure is depicted in FIG. 3 as layer members exploded from the tubular structure 100. A tubular shrinkable sheath 102 overlays a coiled underlying support layer 104. A drive shaft 106 is inserted within a lumen 108 of the underlying support layer. An operating head 110 attaches to the distal end of the tubular structure.

Figure 4:
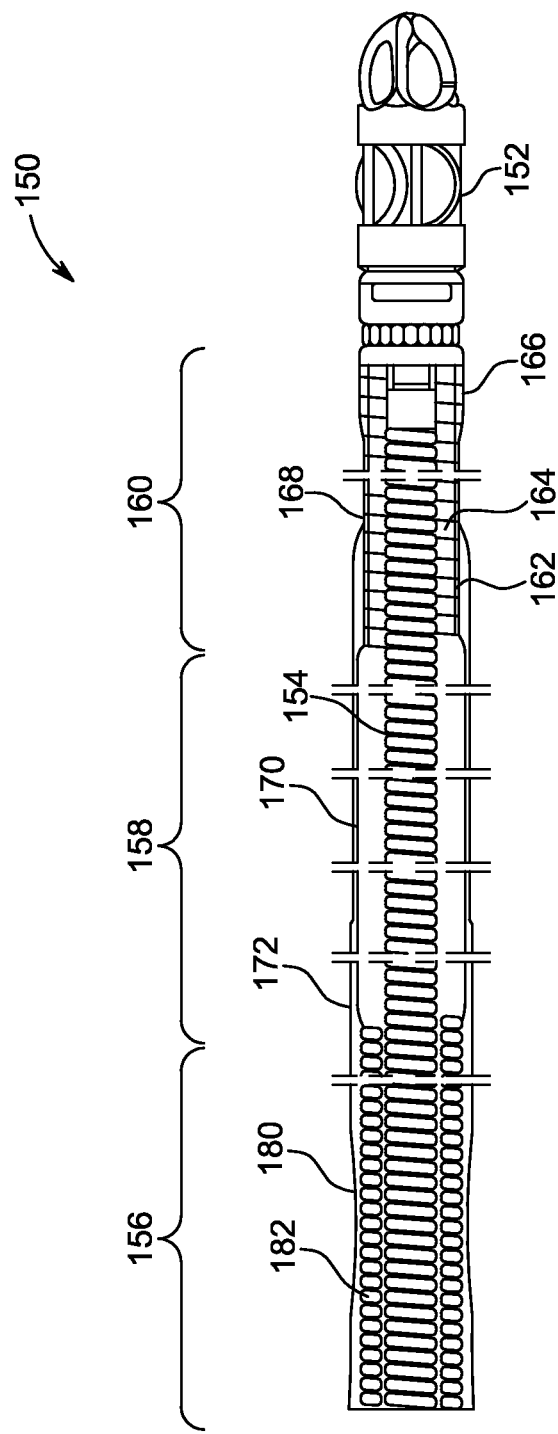
FIG. 4 is a schematic diagram of a cross-section of one embodiment of the tubular structure of the present invention in a catheter having sections of differing characteristics.

FIG. 4 depicts another embodiment of a catheter that includes the multiple construction variations along the length of a tubular structure, such as the variations shown in FIGS. 1A and 1B. The tubular structure 150 is attached to an operating head 152, such as a cutter, at a distal end of the structure. A drive shaft 154 extends within the lumen of the tubular structure. At times, a guidewire also extends within the drive shaft. The catheter generally has a proximal section 156, mid section 158 and distal section 160. Oftentimes, the sections of the catheter have differing characteristics. In some embodiments, the distal section has the most flexibility of the sections, the mid section has less flexibility and the proximal section has the least flexibility. The catheter sections may extend along a variety of lengths of the catheter. For example, from distal to proximal end, the distal section may be about 8.0 cm and the proximal section may be about 25 cm. Of course, the overall length of the catheter and the individual section depends at least on the location of the removal site relative to the insertion site in the body.

The distal section of the catheter may include a tubular structure portion as shown in FIG. 1A. An underlying support layer 162 is provided having coils 164 without gaps and in which the loops of the coil are welded together. A bonding point 166 may be fixedly coupled to the operating head 152, such as by glue. The distal section further may include a highly flexible section 168 proximal to the bonding point 166. The highly flexible section includes a coiled support layer 162 having substantial gaps between loops of the coil element.

In one embodiment, the mid section 158 includes a less flexible area 170 than the distal section, and which does not include a support element. An attachment layer 172 may be included and comprise a tough and non-stick or reduced-stick coating such as polytetrafluorothylene (PFTE) polymer, for example, TEFLON material to permit the catheter to slide easily through the body path. The outer layers may be any thickness, such as 0.001 to 0.005 inch and more commonly the second outer layer is about 0.0020 inch.

The proximal section 156 may be a medium flexibility section, often constructed for added stiffness so that the catheter may be easily axially translated into the body from the proximal end, and yet having some flexibility to allow the catheter to bend and be manipulated at an appropriate angle into the body. Thus, the proximal section is typically somewhat stiffer than the more distal sections of the catheter.

In one embodiment, a support layer 182 and at least one overlying layer 180 is provided. The support layer and the overlying layer that contacts the support layer (i.e. "contacting overlying layer") are only bonded to each other at a single point, such as at the proximal end of the layers. Furthermore, the support layer is provided having a "hard-stacked" support element that does not include substantial gaps when the support layer is straight. Thus, loops of a coil are adjacent to each other. When the proximal section is made to bend, the loops of the coils in the support layer may shift and reposition relative to each other, thereby producing gaps between the loops, to accommodate the bend. In addition, the support layer slips relative to the contacting overlying layer to permit the bending of the structure.

The flexibility of the medium flexibility section without kinking is not restricted by tension between fixed coils. The amount of available by this construction is limited by the inherent flexibility of the material comprising overlying layer more than the flexibility of the support layer. However, although the section is somewhat flexible, the structural integrity is maintained. For example, the medium flexibility of this section may permit the tubular structure at this section to bend around an object that is between 0.75 and 1.50, and more typically about 1.00" radius without kinking.

In still a further embodiment, a triple layer foundation 180 may be provided by the tubular structure. For example, a first outer layer that contacts the underlying support layer 182 and second outer layer around the first outer layer may be provided. In one embodiment, at least one of the outer layers may be braided to provide extra support. The first outer layer may be about 0.0035 inch and the second outer layer.

In one embodiment, a liner may also be provided in at least the proximal section and around at least a portion of the drive shaft to permit a sealing liquid to immerse a flood space between the liner and the drive shaft and/or within the drive shaft, thereby creating a liquid seal around the drive shaft. The liner is typically highly flexible so that the liner follows the contour of the torque tube without adding resistance to the flexing of the catheter.

The catheter shown and described is provided by example and other constructions of catheters with tubular structures are intended within the scope of the present invention. In other embodiments of catheters incorporating the tubular structure, the distal, mid and proximal sections have various constructions of the tubular structure, depending on the application of the catheter. For example, catheters that are useful for treating femoral vessels may include a highly flexible section in both the mid and distal portions of the catheter.

Figure 5:
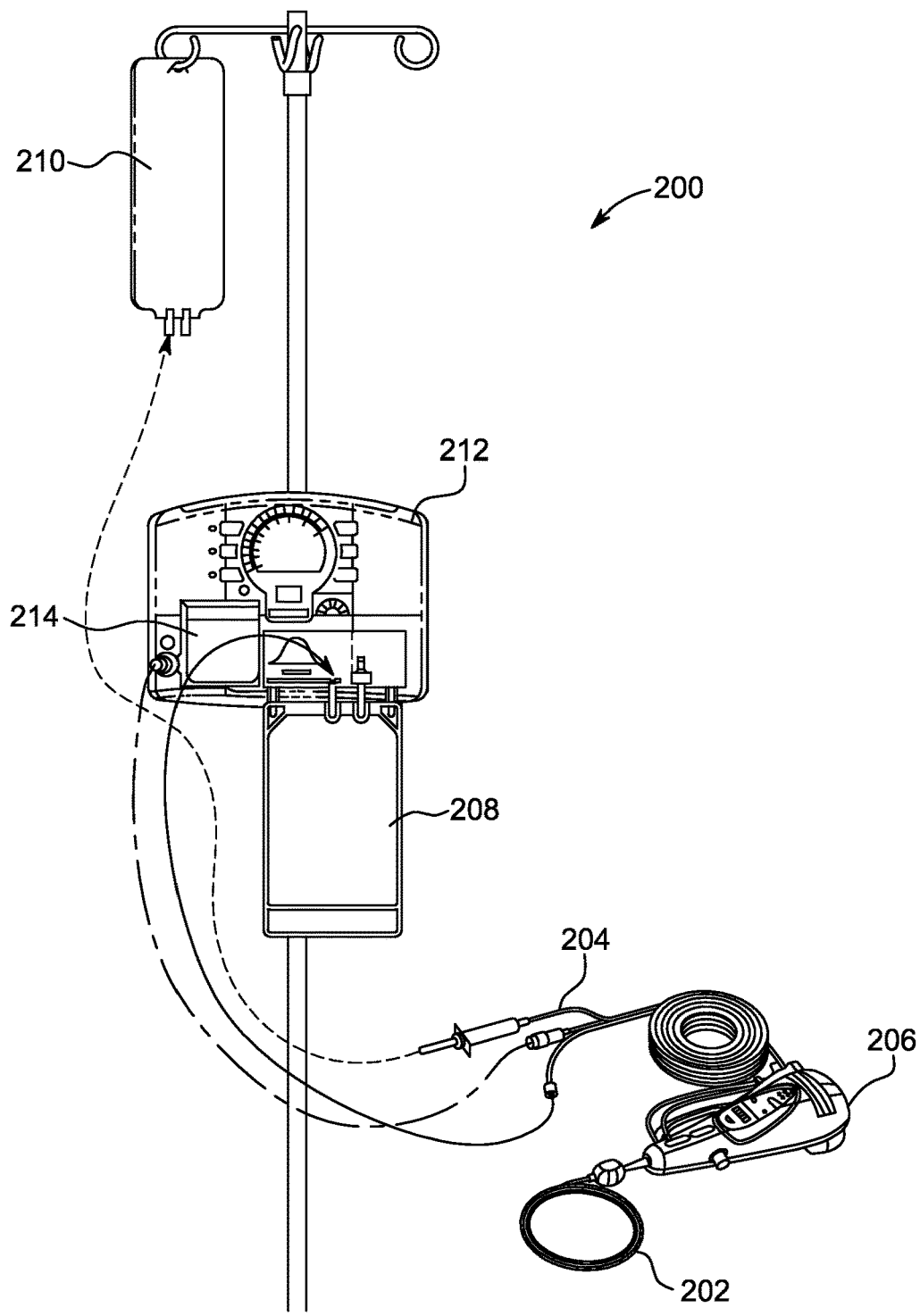
FIG. 5 is a schematic diagram of one medical removal system that may incorporate the present tubular structure, according to the present invention.

The catheter having the tubular structure is often incorporated into a medical device. One example of such a medical device 200 is shown in FIG. 5. A catheter system 202 that comprises an operating head at a distal end and a power source, e.g. drive system, at a proximal end, is provided. Typically, the drive system e.g. a high-speed electric motor, or a pneumatic-powered motor, is included in order to rotate a drive shaft of a catheter 202 incorporating the tubular structure. Oftentimes, the drive shaft may be rotated at high speed of about 500 rpm to 200,000 rpm may be used, more typically about 10,000 to 100,000 rpm and more often about 40,000 rpm, or more. In addition, one or more control systems may be included to direct the speed of rotation and to assist in the operation of the intracorporeal device.

The drive system may be housed within a hand held device 206, e.g. tracking pod. A tubing system 204 extends from the pod 206 to a receiving container 208 that collects fluid and/or particles flowing from the catheter system. The pod may house the drive system, one or more connectors, system controls, etc. An infusate source 210 may also be provided to release fluid into the catheter system, when desired. At the proximal location of the medical device, a console unit 212 may further be provided to receive control information from an operator and/or present operation information to the operator. The console unit 312 may also provide a power source for the motor and an aspiration source. One or more pump(s) 214 may also be provided to provide aspiration for drawing materials from the catheter system and to receiving container 208. In one embodiment, console unit 212 and pump 214 are provided as a re-usable unit. In another embodiment, the hand held tracking pod 206 and control buttons may also be provided as a reusable unit. The catheter system often includes multiple layers of components such as a drive shaft, one or more sheaths, optional guidewire, etc. A more detailed description of one type of medical device in which the tubular structure of the present invention may be used is provided in U.S. Pat. No. 6,565, 588 B1, filed on Nov. 28, 2000.

The methods of producing the tubular structure having the shrinkable sheath generally includes providing a shrinkable tube having an original diameter that is 25% or less of the outer diameter of the underlying layer. Etches are created on at least the interior surface of the sheath. A sheath fabricated from TEFLON material turns from a transparent color to brown when the sheath is sufficiently etched. The underlying layer is inserted into the sheath wherein the underlying layer does not contact the sheath. The sheath is heated such that the sheath shrinks to a second diameter that is 25% or less of the first diameter and the sheath tightly molds around the underlying layer. The second diameter substantially equals the outer diameter of the underlying layer.

The temperature and time for the shrinking depends on the type of shrinkable sheath material employed. For example, a TEFLON PTFE sheath is heated to about 650 degrees F. The heat may be applied by any convenient mechanism, such as a heat gun or placing the tubular structure within an automated heating unit. Oftentimes, the shrunken sheath becomes stiff during the melting process. The outer surface of the shrinkable sheath, having been melted around the underlying layer, may then be rubbed against a rigid surface to break up tension of the sheath and permit high flexibility of the tubular structure. In this manner, friction between the loops of the coil and the sheath caused by the shrinking process is eliminated.

Where the tubular structure includes multiple layers of thermally shrinkable material, such as a shrinkable sheath and shrinkable insert as describe with regard to FIG. 1B, the heat processes for each layer may be independently performed. The shrinkable insert may be melted to the underlying layer and then the outer shrinkable sheath may be melted to the tubular structure.

The present invention has been described above in varied detail by reference to particular embodiments and figures. However, these specifics should not be construed as limitations on the scope of the invention, but merely as illustrations of some of the present embodiments. It is to be further understood that other modifications or substitutions may be made to the described the tubular structure and medical device, as well as methods of their use without departing from the broad scope of the invention. For example, in some embodiments, at least a section of the tubular structure may include additional layers underlying the support layer and/or overlying the thermally shrinkable layer.

I claim:

1. An intracorporeal medical device comprising:
(a) an operating head;
(b) a catheter comprising a tubular structure, the tubular structure comprising:
an overlying layer and a support layer extending through the overlying layer and defining an internal lumen within the tubular structure, wherein the support layer comprises a contiguous coil element, a braid element or a weave element including a plurality of loops, the support layer being fixedly attached to the overlying layer at a bonding point and not attached to the overlying layer along a free portion and wherein the support layer contacts the overlying layer continuously along the remaining length of the free portion and the support layer is slippable relative to the overlying layer along the free portion when the tubular structure is bent; and
(c) a drive shaft attached to the operating head and extending directly within, and rotatable within, the internal lumen of the tubular structure to rotate the operating head with the drive shaft facing the coil element, the braid element or the weave element with no intervening structure therebetween; wherein the drive shaft is rotatable relative to the overlying layer and the support layer.

2. The intracorporeal medical device of claim 1, wherein the loops are moveable to reposition relative to each other as the tubular structure is bent.

3. The intracorporeal medical device of claim 1, wherein the bonding point is at one end of the support layer and the remaining portion of the support layer is the free portion.

4. The intracorporeal medical device of claim 1, wherein the tubular structure is flexible around a 0.75 to 1.50 inch radius object without kinking.

5. The intracorporeal medical device of claim 1, wherein:
the overlying layer is formed as a thermally shrinkable sheath having a plurality of etches on at least its interior surface,
wherein the thermally shrinkable sheath encases and contacts the support layer and the
support layer and the thermally shrinkable sheath are slippable relative to one another along the free portion.

6. The intracorporeal medical device of claim 5, wherein the thermally shrinkable sheath comprises a polytetrafluoroethylene (PTFE) material.

7. The intracorporeal medical device of claim 6, wherein the thermally shrinkable sheath comprises PTFE, TEFLON, fluorinated ethylene propylene (FEP) and/or perfluoroalkoxy polymer resin (PFA).

8. The intracorporeal medical device of claim 5, wherein etches are provided on interior and exterior surfaces of the sheath.

9. The intracorporeal medical device of claim 5, wherein etches are provided across the entire length of the thermally shrinkable sheath surface.

10. The intracorporeal medical device of claim 1, wherein the support layer includes the contiguous coil element, and the contiguous coil element comprises a wire and a plurality of gaps between each loop, the gaps being of sufficient size to resist kinking of the tubular structure.

11. The intracorporeal medical device of claim 10, wherein the length of each gap is about 10-200 percent of the width of the wire.

12. The intracorporeal medical device of claim 10, wherein the tubular structure is flexible around a 0.25 to 0.50 inch radius object without kinking.

13. The intracorporeal medical device of claim 12, wherein the overlying layer is formed as a thermally shrinkable sheath is bonded to the support layer at a bonding point located at one end of the thermally shrinkable sheath and the thermally shrinkable sheath is capable of slipping along the support layer as the tubular structure is bent.

14. The intracorporeal medical device of claim 1, wherein:
the overlying layer is formed as a thermally shrinkable sheath having a plurality of etches on at least its interior surface, the thermally shrinkable sheath encasing at least a portion of the support layer by heat-reduction of 25 percent or less of an original diameter of the thermally shrinkable sheath.

15. The intracorporeal medical device of claim 14, wherein the thermally shrinkable sheath comprises a polytetrafluoroethylene (PTFE) material.

16. The intracorporeal medical device of claim 15, wherein the thermally shrinkable sheath comprises PTFE, TEFLON, fluorinated ethylene propylene (FEP) and/or perfluoroalkoxy polymer resin (PFA).

17. The intracorporeal medical device of claim 16, wherein the support layer includes the contiguous coil element, and the contiguous coil element comprises a wire and a plurality of gaps between each loop, the gaps being of sufficient size to resist kinking of the tubular structure.

18. The intracorporeal medical device of claim 17, wherein the length of each gap is about 10-200 percent of the width of the wire.

19. The intracorporeal medical device of claim 1, wherein at least a portion of the support layer includes gaps between each of the plurality of loop of the coiled element, the gaps being of sufficient size to resist kinking of the tubular structure.

20. The intracorporeal medical device of claim 1, further comprising a drive system and a control system to direct rotation of the drive shaft.

21. The intracorporeal medical device of claim 1, wherein the operating head comprises a cutter.

22. The intracorporeal medical device of claim 1, wherein the catheter comprises a proximal section having the least flexibility, a mid section and a distal section having the most flexibility and the distal section comprises the tubular structure.

23. The intracorporeal medical device of claim 22, wherein the mid section includes a less flexible area that does not incorporate a support layer.

24. The intracorporeal medical device of claim 1, wherein the support layer of the tubular structure is welded to the operating head.

25. The intracorporeal medical device of claim 1, wherein the support layer incorporates a less flexible support element at or near the bonding point.

* * * * *